United States Patent
Wingen et al.

(10) Patent No.: US 6,811,832 B2
(45) Date of Patent: Nov. 2, 2004

(54) ORTHO SUBSTITUTED BENZALDEHYDES, PREPARATION THEREOF AND USE THEREOF

(75) Inventors: Rainer Wingen, Hattersheim (DE); Wolfgang Schmidt, Dreieich (DE)

(73) Assignee: Clariant GmbH, Frankfurt (DE)

(*) Notice: Subject to any disclaimer, the term of this patent is extended or adjusted under 35 U.S.C. 154(b) by 176 days.

(21) Appl. No.: 09/852,552

(22) Filed: May 10, 2001

(65) Prior Publication Data

US 2001/0050352 A1 Dec. 13, 2001

(30) Foreign Application Priority Data

May 10, 2000 (DE) .......................................... 100 22 661

(51) Int. Cl.$^7$ ...................... C09K 19/32; C07C 25/24; C07C 45/61; C07C 47/55
(52) U.S. Cl. .................. 428/1.1; 252/299.62; 568/437; 570/128
(58) Field of Search ................................ 570/191, 187, 570/141, 128; 252/299.01, 299.62; 568/437; 428/1.1

(56) References Cited

U.S. PATENT DOCUMENTS

| | | |
|---|---|---|
| 3,428,647 A | 2/1969 | Braun et al. |
| 3,856,504 A | 12/1974 | Dickson |
| 3,982,020 A | 9/1976 | Houlihan et al. |
| 4,558,166 A | 12/1985 | Baasner et al. |
| 4,902,814 A | 2/1990 | Whittle |
| 5,648,021 A | 7/1997 | Wingen et al. |

FOREIGN PATENT DOCUMENTS

| | | |
|---|---|---|
| DE | 33 10 953 | 9/1984 |
| DE | 195 00 768 | 9/1995 |
| EP | 0 174 131 | 3/1986 |
| EP | 0 211 584 | 2/1987 |
| EP | 0 271 240 | 6/1988 |
| EP | 0 289 942 | 11/1988 |
| EP | 0 568 289 | 11/1993 |
| FR | 1 514 517 | 1/1968 |
| WO | 98/14433 | 4/1998 |
| WO | 01/68653 | 9/2001 |

OTHER PUBLICATIONS

CAPLUS 2002: 538148.*
CAPLUS 2001: 693326.*
Abstract for PCT application 98/34111, 1998.
Abstract OD–89623/85 for JP–143237, Feb. 27, 1985.
Abstract OD–0838/86 for DE 3422915, Dec. 19, 1985.
Abstract OD–238142/88 for JP–315664, Jul. 14, 1988.
Abstract OD–316228/88 for JP–111978, Nov. 9, 1988.
Abstract OD–001087/90 for DE 820979, Dec. 27, 1989.
Abstract for Banks, R., et al., "Halex" Fluorination of Chlorinted Benzaldehydes and Benzoyl Chlorides, J. Fluorine Chem., 46 (1990) 3, p. 529–537.
Kumar, S., "A New and Concise Synthesis of 3–Hydroxybenzo[c]phenanthrene and 12–Hydroxybenzo[g]chrysene, Useful Intermediates for the Synthesis of the Fjord–Region Diol Epoxides of Benzo[c]phenanthrene and Benzo{g chrysene," J. Org.Chem. 1997, 62, 8535–8539.
Abstract for Kanie et al., Bull. Chem. Soc. Jpn. 2000, 73, 471.

\* cited by examiner

Primary Examiner—Shean C. Wu
(74) Attorney, Agent, or Firm—Scott E. Hanf; Anthony A. Bisulca

(57) ABSTRACT

Compounds of the formula (I):

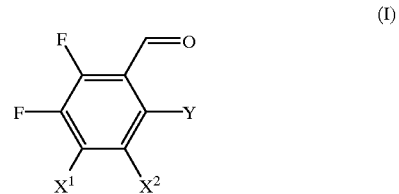

in which $X^1$=H or F, $X^2$=H or F, and Y=Cl, Br or I, are prepared by reacting, in a solvent or solvent mixture at a temperature below –60° C., a halobenzene of the formula (II) with an organic lithium compound and then with a formyl equivalent of the formula (III):

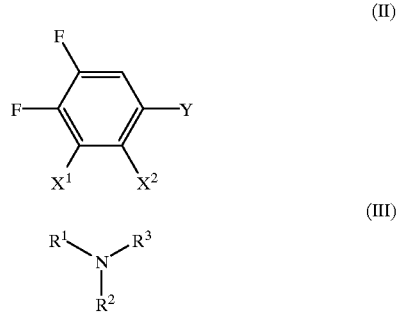

and may be used as starting materials for preparing agrochemicals, electronic materials and pharmaceuticals.

13 Claims, No Drawings

ORTHO SUBSTITUTED BENZALDEHYDES, PREPARATION THEREOF AND USE THEREOF

BACKGROUND OF THE INVENTION

Benzaldehydes having ortho halogen substituents or having a total of up to five halogen substituents are extensively described in the chemical literature as starting materials for the synthesis of active substances (e.g. EP-A-0 174 131, EP-A-0 271 240, EP-A-0 289 942, FR-A-1 514 517, U.S. Pat. No. 3,856,504, U.S. Pat. No. 3,982,020, U.S. Pat. No. 4,902,814) or generally as an intermediate (DE-A 3310 953). Aldehydes which have a chlorine, bromine or iodine substituent in one ortho position and a fluorine substituent in the other, are known in the form of 2-chloro-6-fluorobenzaldehyde, 2-bromo-6-fluorobenzaldehyde and 2-fluoro-6-iodobenzaldehyde. However, there is a need for compounds having a plurality of fluorine substituents and additional functionalities, since fluorination or a different degree of fluorination very often enhances the activity of agrochemicals or pharmaceuticals by changing the lipophilicity and/or dipole moment (Kanie et al., Bull. Chem. Soc. Jpn. 2000, 73, 471).

SUMMARY OF THE INVENTION

Benzaldehydes having a plurality of fluorine substituents, one of which is ortho to the aldehyde function, and an ortho halogen substituent (which is not fluorine), are unknown, although some of these compounds can be constructed from generic formulations in the above mentioned references.

DESCRIPTION OF THE PREFERRED EMBODIMENTS

The invention accordingly provides ortho substituted benzaldehydes of the formula (I):

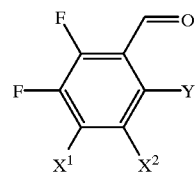

in which $X^1$, $X^2$ and Y have the following meanings:
$X^1$=H or F
$X^2$=H or F
Y=Cl, Br or I.
Preference is given to compounds in which
a) $X^1$ and $X^2$ are H Y is Cl or Br; or
b) $X^1$ is F, $X^2$ is H Y is Cl or Br; or
c) $X^1$ and $X^2$ are F Y is Cl or Br;
in particular
2-chloro-5,6-difluorobenzaldehyde
2-bromo-5,6-difluorobenzaldehyde
2-chloro-4,5,6-trifluorobenzaldehyde
2-bromo-4,5,6-trifluorobenzaldehyde.

The invention furthermore provides a process for preparing the compounds of the formula (I), which comprises reacting, in a solvent or solvent mixture at a temperature which does not promote arine formation, a halobenzene of the formula (II), in which Y, $X^1$ and $X^2$ are as defined in (I), with an organic lithium compound. The molar ratio of lithium compound to starting material (II) is preferably from 1:1 to 1.2:1. The resulting lithium compound is then, again at a temperature which does not promote arine formation, reacted with a formyl equivalent of the formula (III) and subsequently hydrolyzed to give (I). The molar ratio of (II) to (III) is preferably from 1:1 to 1:2.

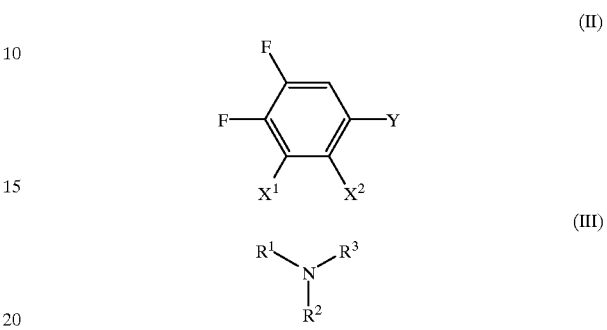

In (III), $R^1$ is an alkyl radical having 1 to 6 carbon atoms, a trimethylsilyl radical or (substituted or unsubstituted) phenyl, $R^2$ is an alkyl radical having 1 to 6 carbon atoms, a trimethylsilyl radical or (substituted or unsubstituted) phenyl, and $R^3$ is —CH(=O) or —CH(OR$^4$)$_2$; $R^1$ and $R^2$, together with the nitrogen atom, may also be part of a five- to seven-membered ring. $R^4$ is an alkyl radical having 1 to 4 carbon atoms.

The reaction of (II) with the organic lithium compound is preferably carried out at a temperature below −60° C., very particularly preferably below −70° C., in particular at a temperature in the range from −70° C. to −110° C. Typical reaction times are from 1 to 8 hours. When the reaction is complete (detectable e.g. by DC or GC), the reaction mixture is slowly warmed to −25 to −15° C. and carefully hydrolyzed with water. The mixture is then acidified to pH 1 to 5 using hydrochloric acid and extracted with a suitable solvent (e.g. tert-butyl methyl ether, dichloromethane, ethyl acetate, toluene). The extracts of the organic phase are combined and dried, for example with sodium sulfate. The solvent can be removed under reduced pressure to give the desired ortho substituted benzaldehyde of the formula (III). If necessary, the product can be purified by chromatography, distillation or crystallization or a combination thereof. Typical yields are in the range from 50 to 80%, based on (II). The organic lithium compound is preferably the lithium compound of a secondary amine, preferably having bulky substituents. Particular preference is given to lithium diisopropylamide, lithium 2,2,6,6-tetramethylpiperidide, lithium dicyclohexylamide, lithium cyclohexylisopropylamide or lithium bis(trimethylsilyl)amide. Very particular preference is given to lithium 2,2,6,6-tetramethylpiperidide. For those compounds of the formula (II) in which Y is Cl, the organic lithium compound is an alkyllithium compound or the lithium compound of a secondary amine; preference is given to n-butyllithium. If desired, potassium tert-butylate may be added to improve activation.

In a preferred embodiment, Y in formula (II) is Br. It may be advantageous to add activators or selectivity modifiers to the reaction mixture, e.g. tetramethylethylenediamine or potassium tert-butylate (the latter being preferred for those compounds of the formula (II) in which Y is Cl).

The formyl equivalent of the formula (III) is preferably N,N-dimethylformamide, N,N-diethylformamide, N,N-dipropylformamide, N,N-diisopropylformamide, N,N-dibutylformamide, N-formylpyrrolidine, N-formylmorpholine, N-formylpiperidine, dimethylformamide dialkylacetal, N-methylformanilide, N-ethylformanilide or N,N-bis-(trimethylsilyl)-formamide. The formyl equivalent of the formula (III) is very particular preferably N,N-dimethylformamide.

Suitable solvents for the purposes of the invention are aprotic solvents, for example ethers such as tetrahydrofuran, 1,2-dimethoxyethane, 1,4-dioxane, diethyl ether, or hydrocarbons such as hexane, cyclohexane, heptane, pentane, or mixtures of aprotic solvents.

The reaction of (II) with the organic lithium compound can also be carried out in the presence of the compound (III) so that lithium derivative formed in situ from (II) can react directly with (III). To this end, it may be necessary and advantageous to carry out the reaction above –60° C., e.g. in the range from –20 to +25° C.

The invention furthermore provides the use of compounds of the formula (I) as starting materials for preparing agrochemicals, electronic materials, in particular liquid crystals, and pharmaceuticals. The compounds of the formula (I) are particularly suitable for these purposes, as both the aldehyde function (e.g. via Wittig reaction, reduction to give the benzylalcohol, condensation with C—H, N—H or S—H compounds) and the halogen function (which is herein taken to mean the function of the substituent Y) (e.g. via Suzuki coupling, Grignard reaction, Heck reaction) are available for reactions, and it is possible, under particular conditions in the case of those compounds or products derived therefrom in which $X^1$ is F, very particularly in the case of those compounds or products derived therefrom in which $X^1$ and $X^2$ are F, to utilize the reactivity of a difluoroaromatic compound (e.g. via ortho metallation) or trifluoroaromatic compound (e.g. via ortho metallation or aromatic nucleophilic substitution) or tetrafluoroaromatic compound (e.g. via aromatic nucleophilic substitution).

EXAMPLES

Example 1

2-Bromo-5,6-difluorobenzaldehyde

A solution of 152 mmol of 2,2,6,6-tetramethylpiperidine and 152 mmol of n-butyllithium (1.6 M solution in n-hexane) in 280 ml of dry tetrahydrofuran is admixed with 145 mmol of 1-bromo-3,4-difluorobenzene at –75° C. This temperature is maintained for 4 hours, and then 174 mmol of DMF are added dropwise. The reaction mixture is then slowly thawed, hydrolyzed with water at –20° C., acidified using hydrochloric acid and extracted with tert-butyl methyl ether. The combined organic extracts are washed with saturated sodium chloride solution and dried using sodium sulfate. The solvent is removed under reduced pressure, and the raw product is purified by chromatography over silica gel (eluent: dichloromethane/n-heptane 1:1) and recrystallization from n-heptane, yielding 18 g (56%) of 2-bromo-5,6-difluorobenzaldehyde in the form of slightly yellow crystals.—M.p.: 40–43.5° C.—$^1$H-NMR (400 MHz, CDCl$_3$/TMS): δ=10.31 (dd, $^4J_{(HF)}$=2 Hz, $^5J_{(HF)}$=1.5 Hz, 1 H, CHO), 7.45 (ddd, $^3J_{(HH)}$=9 Hz, $^4J_{(HF)}$=4 Hz, $^5J_{(HF)}$=2 Hz, 1 H, H$_{ar}$), 7.28 (ddd, $^3J_{(HH)}$=9 Hz, $^3J_{(HF)}$=9 Hz, $^4J_{(HF)}$=8 Hz, 1 H, H$_{ar}$).—$^{19}$F-NMR (376.5 MHz, $^1$H broad-band decoupled, CDCl$_3$/CFCl$_3$): δ=–136.4 (d, $^3J$=19.2 Hz), –139.2 (d, $^3J$=19.2 Hz).

Example 2

2-Bromo-4,5,6-trifluorobenzaldehyde can be obtained similarly to Example 1 starting from 1-bromo-3,4,5-trifluorobenzene—$^1$H-NMR (400 MHz, CDCl$_3$/TMS): δ=10.24 (dd, $^4J_{(HF)}$=1.5 Hz, $^5J_{(HF)}$=1 Hz, 1 H, CHO), 7.38 (ddd, $^3J_{(HH)}$=9 Hz, $^4J_{(HF)}$=6 Hz, $^5J_{(HF)}$=2 Hz, 1 H, H$_{ar}$).—$^{19}$F-NMR (376.5 MHz, $^1$H broad-band decoupled, CDCl$_3$/CFCl$_3$): δ=–123.4 (dd, $^3J$=20 Hz and 13 Hz), –135.9 (dd, $^3J$=19 Hz and 13 Hz), –158.0 (dd, $^3J$=20 Hz and 19 Hz).

Example 3

2-Chloro-5,6-difluorobenzaldehyde can be obtained similarly to Example 1 starting from 1-chloro-3,4-difluorobenzene

Example 4

2-Bromo-3,4,5,6-tetrafluorobenzaldehyde can be obtained similarly to Example 1 starting from 1-bromo-2,3,4,5-tetrafluorobenzene

Example 5

2-Chloro-3,4,5,6-tetrafluorobenzaldehyde can be obtained similarly to Example 1 starting from 1-chloro-2,3,4,5-tetrafluorobenzene.

Example 6

2-iodo-5,6-difluorobenzaldehyde can be obtained similarly to Example 1 starting from 3,4-difluoroiodobenzene

Application Example 1

2-bromo-5,6-difluorobenzaldehyde is reacted with 4-pentylphenylboronic acid in the presence of a Pd catalyst to give 3,4-difluoro-4'-pentylbiphenyl-2-carbaldehyde. This compound is reacted with trimethylsulfonium iodide, to give 3,4-difluoro-2-(oxiran-2-yl)-4'-pentyl-biphenyl. Without further purification, this compound is converted into 1,2-difluoro-7-pentylphenanthrene in the presence of BF$_3$ etherate. The raw product is purified by the procedure typical for this type of liquid-crystal materials (cf. DE-A 195 00 768), yielding 1,2-difluoro-7-pentylphenanthrene in the form of colorless crystals. Kumar, J. Org. Chem. 1997, 62, 8535–8539 discloses the coupling of boronic acid compounds with a bromo compound having aldehyde functionality.

What is claimed is:

1. A compound of the formula (I):

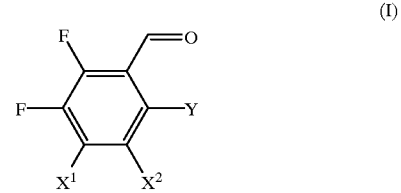

in which $X^1$, $X^2$ and Y have the following meanings:
$X^1$ is H or F
$X^2$ is H or F
Y is Cl, Br or I.

2. The compound as claimed in claim 1, wherein:
a) $X^1$ and $X^2$ are H
 Y is Cl or Br
b) $X^1$ is F, $X^2$ is H
 Y is Cl or Br
c) $X^1$ and $X^2$ are F
 Y is Cl or Br.

3. A process for preparing a compound as claimed in claim 1, which comprises reacting, in a solvent or solvent mixture at a temperature below −60° C., a halobenzene of the formula (II), in which Y, $X^1$ and $X^2$ are as defined in claim 1, with an organic lithium compound and then with a formyl equivalent of the formula (III):

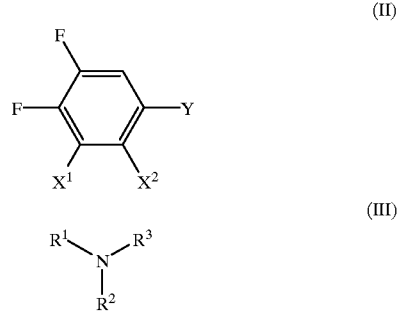

followed by hydrolysis, where in formula (III) $R^1$ is an alkyl radical having 1 to 6 carbon atoms, a trimethylsilyl radical or (substituted or unsubstituted) phenyl, $R^2$ is an alkyl radical having 1 to 6 carbon atoms, a trimethylsilyl radical or (substituted or unsubstituted) phenyl, and $R^3$ is —CH (=O) or —CH(OR$^4$)$_2$, where $R^1$ and $R^2$, together with the nitrogen atom, may also be part of a five- to seven-membered ring and $R^4$ is an alkyl radical having 1 to 4 carbon atoms.

4. The process as claimed in claim 3, wherein the temperature is below −70° C.

5. The process as claimed in claim 3, wherein said compound of the formula (III) is dimethylformamide or diethylformamide.

6. The process as claimed in claim 3, wherein said organic lithium compound is lithium 2,2,6,6-tetramethylpiperidide or lithium diisopropylamide or, when Y=Cl, is alkyl-lithium.

7. The process as claimed in claim 3, wherein activators or selectivity modifiers, in particular tetramethylenediamine or potassium tert-butylate, are added to the reaction mixture.

8. The process as claimed in claim 3, wherein said compound of the formula (II) is reacted with said organic lithium compound in the presence of compounds of the formula (III).

9. The process as claimed in claim 8, wherein the reaction is carried out at a temperature in the range from −20 to +25° C.

10. The process as claimed in claim 3, wherein said compound of the formula (I) is obtained in a yield in the range from 50 to 80%.

11. A method for preparing agrochemicals, electronic materials and pharmaceuticals which contains the step of:
   providing a compound as claimed in claim 1 as a starting material.

12. A method of preparing electronic materials as claimed in claim 11, wherein said electronic materials are components of liquid-crystalline mixtures.

13. A method of preparing components of liquid-crystalline mixtures as claimed in claim 12, wherein said liquid-crystalline mixtures contain components which are phenanthrene derivatives.

* * * * *